(12) United States Patent
Valik et al.

(10) Patent No.: US 10,604,537 B2
(45) Date of Patent: Mar. 31, 2020

(54) SOLID STATE FORMS OF IXAZOMIB CITRATE

(71) Applicant: TEVA PHARMACEUTICALS INTERNATIONAL GMBH, Jona (CH)

(72) Inventors: Martin Valik, Male Hostice (CZ); Roman Gabriel, Olomouc (CZ); Pavel Vraspir, Rymarov (CZ); David Lukas, Blovice (CZ)

(73) Assignee: TEVA PHARMACEUTICALS INTERNATIONAL GMBH, Jona (CH)

( * ) Notice: Subject to any disclaimer, the term of this patent is extended or adjusted under 35 U.S.C. 154(b) by 0 days.

(21) Appl. No.: 16/309,177

(22) PCT Filed: Jun. 8, 2017

(86) PCT No.: PCT/US2017/036482
§ 371 (c)(1),
(2) Date: Dec. 12, 2018

(87) PCT Pub. No.: WO2017/222819
PCT Pub. Date: Dec. 28, 2017

(65) Prior Publication Data
US 2019/0330243 A1    Oct. 31, 2019

Related U.S. Application Data

(60) Provisional application No. 62/438,073, filed on Dec. 22, 2016, provisional application No. 62/352,787, filed on Jun. 21, 2016.

(51) Int. Cl.
*C07F 5/02* (2006.01)
(52) U.S. Cl.
CPC .......... *C07F 5/025* (2013.01); *C07B 2200/13* (2013.01)

(58) Field of Classification Search
CPC .............................. C07F 5/025; C07B 2200/13
USPC ......................................................... 549/213
See application file for complete search history.

(56) References Cited

U.S. PATENT DOCUMENTS 5,384,410 A * 1/1995 Kettner ................... C07F 5/025
530/326
8,859,504 B2   10/2014 Elliott et al.

FOREIGN PATENT DOCUMENTS

| WO | 2009154737 A1 | 12/2009 |
| WO | 2016155864 A1 | 10/2016 |
| WO | 2016165677 A1 | 10/2016 |
| WO | 2017046815 A1 | 3/2017 |

OTHER PUBLICATIONS

International Council for Harmonisation of Technical Requirements for Pharmaceuticals for Human Use; "Impurities: Guideline for Residual Solvents Q3C(R6)"; Step 4 version: Oct. 20, 2016, 40 pages.
International Search Report for International Application No. PCT/US2017/036482, International Filing Date Jun. 8, 2017, dated Mar. 19, 2018, 6 pages.
Written Opinion for International Application No. PCT/US2017/036482, International Filing Date Jun. 8, 2017, dated Mar. 19, 2018, 9 pages.

* cited by examiner

*Primary Examiner* — Rita J Desai
(74) *Attorney, Agent, or Firm* — Cantor Colburn LLP (57) ABSTRACT

The present disclosure encompasses solid state forms of Ixazomib Citrate and pharmaceutical compositions thereof. Also disclosed are processes for preparation of Ixazomib Citrate.

16 Claims, 7 Drawing Sheets

Figure 1. X-ray powder diffraction pattern of form G of Ixazomib Citrate.

Figure 2. X-ray powder diffraction pattern of form A of Ixazomib Citrate.

Figure 3. X-ray powder diffraction pattern of form 1A of Ixazomib Citrate.

Figure 4. X-ray powder diffraction pattern of form 1B of Ixazomib Citrate.

Figure 5. X-ray powder diffraction pattern of form F of Ixazomib Citrate.

Figure 6. X-ray powder diffraction pattern of form 2 of Ixazomib Citrate, obtained by example 5.

Figure 7. X-ray powder diffraction pattern of form 1 of Ixazomib Citrate, obtained by example 12.

SOLID STATE FORMS OF IXAZOMIB CITRATE

FIELD OF THE DISCLOSURE

The present disclosure encompasses solid state forms of Ixazomib Citrate and pharmaceutical compositions thereof. The invention further relates to processes for preparation of Ixazomib Citrate.

BACKGROUND OF THE DISCLOSURE

Ixazomib Citrate is the citrate ester of Ixazomib.

NINLARO® is described in the prescribing information as 1,3,2-dioxaborolane-4,4-diacetic acid, 2-[(1R)-1-[[2-[(2,5dichlorobenzoyl)amino]acetyl]amino]-3-methylbutyl]-5-oxo, having the following chemical structure:

Compound 1

NINLARO® is a proteasome inhibitor indicated in combination with lenalidomide and dexamethasone for the treatment of patients with multiple myeloma who have received at least one prior therapy.

Solid state forms of Ixazomib Citrate and processes for preparation thereof are described in WO 2009/154737 as well as in WO 2016/155684, WO 2016/165677 and WO 2017/046815.

Polymorphism, the occurrence of different crystalline forms, is a property of some molecules and molecular complexes. A single molecule may give rise to a variety of polymorphs having distinct crystal structures and physical properties like melting point, thermal behaviors (e.g., measured by thermogravimetric analysis—"TGA", or differential scanning calorimetry—"DSC"), X-ray diffraction pattern, infrared absorption fingerprint, and solid state (13C) NMR spectrum. One or more of these techniques may be used to distinguish different polymorphic forms of a compound.

Different salts and solid state forms (including solvated forms) of an active pharmaceutical ingredient may possess different properties. Such variations in the properties of different salts and solid state forms and solvates may provide a basis for improving formulation, for example, by facilitating better processing or handling characteristics, changing the dissolution profile in a favorable direction, or improving stability (polymorph as well as chemical stability) and shelf-life. These variations in the properties of different salts and solid state forms may also offer improvements to the final dosage form, for instance, if they serve to improve bioavailability. Different salts and solid state forms and solvates of an active pharmaceutical ingredient may also give rise to a variety of polymorphs or crystalline forms, which may in turn provide additional opportunities to assess variations in the properties and characteristics of a solid active pharmaceutical ingredient.

Discovering new solid state forms and solvates of a pharmaceutical product may yield materials having desirable processing properties, such as ease of handling, ease of processing, storage stability, and ease of purification or as desirable intermediate crystal forms that facilitate conversion to other polymorphic forms. New solid state forms of a pharmaceutically useful compound can also provide an opportunity to improve the performance characteristics of a pharmaceutical product. It enlarges the repertoire of materials that a formulation scientist has available for formulation optimization, for example by providing a product with different properties, e.g., a different crystal habit, higher crystallinity, or polymorphic stability, which may offer better processing or handling characteristics, improved dissolution profile, or improved shelf-life (chemical/physical stability). For at least these reasons, there is a need for additional solid state forms (including solvated forms) of Ixazomib Citrate.

SUMMARY OF THE DISCLOSURE

The present disclosure provides solid state forms of Ixazomib Citrate, processes for preparation thereof, and pharmaceutical compositions thereof. These solid state forms can be used to prepare other solid state forms of Ixazomib Citrate, Ixazomib Citrate salts and solid state forms thereof.

The present disclosure provides solid state forms of Ixazomib Citrate for use in the preparation of pharmaceutical compositions comprising Ixazomib Citrate.

The present disclosure also encompasses the use of the Ixazomib Citrate solid state forms of the present disclosure for the preparation of pharmaceutical compositions of Ixazomib Citrate.

The present disclosure comprises processes for preparing the above mentioned pharmaceutical compositions. The processes comprise combining the Ixazomib Citrate solid state forms with at least one pharmaceutically acceptable excipient.

The solid state forms and the pharmaceutical compositions of Ixazomib Citrate of the present disclosure can be used as medicaments, particularly for the treatment of multiple myeloma.

The present disclosure also provides methods of treating multiple myeloma comprising administering a therapeutically effective amount of a Ixazomib Citrate solid state form of the present disclosure, or at least one of the above pharmaceutical compositions, to a subject in need of the treatment.

DETAILED DESCRIPTION OF THE DISCLOSURE

The present disclosure encompasses solid state forms of Ixazomib Citrate. Solid state properties of Ixazomib Citrate can be influenced by controlling the conditions under which the Ixazomib Citrate is obtained in solid form.

The present disclosure further encompasses novel processes for preparation of Ixazomib Citrate from 2,5-Dichloro-N-[2-[[(1R)-1-[(3aS,4S,6S,7aR)-hexahydro-3a,5,5-trimethyl-4,6-methano-1,3,2-benzodioxaborol-2-yl]-3-methylbutyl]amino]-2-oxoethyl]benzamide.

WO 2009/154737 discloses a two steps process wherein 2,5-Dichloro-N-[2-[[(1R)-1-[(3aS,4S,6S,7aR)-hexahydro-3a,5,5-trimethyl-4,6-methano-1,3,2-benzodioxaborol-2-yl]-3-methylbutyl]amino]-2-oxoethyl]benzamide is firstly hydrolyzed using equimolar amounts of HCl and in the presence of excess of isobutylboronic acid (as a boronic acid acceptor for pinanediol leaving group) in a two phase system. The process includes a step of isolation of the hydrolyzed product which is thereafter converted to Ixazomib Citrate in a separate condensation reaction with citric acid.

WO 2016/155684 discloses a one step process wherein 2,5-Dichloro-N-[2-[[(1R)-1-[(3aS,4S,6S,7aR)-hexahydro-3a,5,5-trimethyl-4,6-methano-1,3,2-benzodioxaborol-2-yl]-3-methylbutyl]amino]-2-oxoethyl]benzamide is directly converted to Ixazomib Citrate. Elimination of pinanediol group is performed by using boric acid instead of isobutylboronic acid. The acid environment necessary for the elimination is provided by citric acid which reacts at the same time with the product of elimination to form Ixazomib Citrate; and presence of mineral acid is not required. This process is performed in a one phase system, however the combination of citric acid and boronic acid in the reaction mixture may result in the formation of citrato or bis(citrato) borate impurities which are difficult to determine/quantify.

Further, WO 2016/165677 and WO 2017/046815 disclose crystallization of Ixazomib Citrate in the presence of alcoholic solvents which may esterify the citric acid and thereby result in formation of more impurities.

In contrast to the prior art processes, the process of the present disclosure uses only catalytic amounts of mineral acid, and avoids the use of organic boronic acid or boric acid as acceptors in the pinanediol elimination step. Instead, according to the present disclosure, the elimination reaction is performed in the presence of a ketone solvent that serves also as the acceptor of the pinanediol leaving group. Further according to the process of the present disclosure, Ixazomib Citrate can be directly isolated in high yield from the one pot reaction in the one phase system, by direct crystallization that does not require addition of anti-solvent or solvent exchange. Therefore, the processes of the present disclosure can be easily adapted to production in an industrial scale, i.e., greater than 1 kilogram scale.

Prior art Ixazomib Citrate/Ixazomib Citrate pharmaceutical compositions comprising form 2 of Ixazomib Citrate may typically either contain high levels of residual solvents or are provided as mixtures with other forms, such as form 1.

The process of the present disclosure provides Ixazomib Citrate, preferably form 2 of Ixazomib Citrate, which contains low levels of residual solvents and is substantially free of any other forms of Ixazomib Citrate, or of specified forms of Ixazomib Citrate, for example form 1.

In some embodiments, the crystalline forms of Ixazomib Citrate of the disclosure are substantially free of any other forms of Ixazomib Citrate, or of specified polymorphic forms of Ixazomib Citrate, respectively.

As used herein, by "substantially free" it is meant that the solid state forms of the present disclosure contain 20% (w/w) or less of polymorphs, or of a specified polymorph of Ixazomib Citrate. According to some embodiments, the salts and solid state forms of the present disclosure contain 10% (w/w) or less, 5% (w/w) or less, 2% (w/w) or less, or 1% (w/w) or less of polymorphs, or of a specified polymorph of Ixazomib Citrate. In other embodiments, solid state forms of Ixazomib Citrate of the present disclosure contain from 1% to 20% (w/w), from 5% to 20% (w/w), or from 5% to 10% (w/w) of any solid state forms or of a specified polymorph of Ixazomib Citrate.

Depending on which other solid state forms comparison is made, the crystalline forms of Ixazomib Citrate of the present disclosure have advantageous properties selected from at least one of the following: chemical purity, flowability, solubility, dissolution rate, morphology or crystal habit, stability—such as chemical stability as well as thermal and mechanical stability with respect to polymorphic conversion, stability towards dehydration and/or storage stability, low content of residual solvent, a lower degree of hygroscopicity, flowability, and advantageous processing and handling characteristics such as compressibility, and bulk density.

A solid state form, such as a crystal form or amorphous form, may be referred to herein as being characterized by graphical data "as depicted in" or "as substantially depicted in" a Figure. Such data include, for example, powder X-ray diffractograms and solid state NMR spectra. As is well-known in the art, the graphical data potentially provides additional technical information to further define the respective solid state form (a so-called "fingerprint") which cannot necessarily be described by reference to numerical values or peak positions alone. In any event, the skilled person will understand that such graphical representations of data may be subject to small variations, e.g., in peak relative intensities and peak positions due to certain factors such as, but not limited to, variations in instrument response and variations in sample concentration and purity, which are well known to the skilled person. Nonetheless, the skilled person would readily be capable of comparing the graphical data in the Figures herein with graphical data generated for an unknown crystal form and confirm whether the two sets of graphical data are characterizing the same crystal form or two different crystal forms. A crystal form of Ixazomib Citrate referred to herein as being characterized by graphical data "as depicted in" or "as substantially depicted in" a Figure will thus be understood to include any crystal forms of Ixazomib Citrate characterized with the graphical data having such small variations, as are well known to the skilled person, in comparison with the Figure.

As used herein, and unless stated otherwise, the term "anhydrous" in relation to crystalline forms of Ixazomib Citrate, relates to a crystalline form of Ixazomib Citrate which does not include any crystalline water (or other solvents) in a defined, stoichiometric amount within the crystal. Moreover, an "anhydrous" form would typically not contain more than 1% (w/w), of either water or organic solvents as measured for example by TGA.

The term "solvate," as used herein and unless indicated otherwise, refers to a crystal form that incorporates a solvent in the crystal structure. When the solvent is water, the solvate is often referred to as a "hydrate." The solvent in a solvate may be present in either a stoichiometric or in a non-stoichiometric amount.

As used herein, and unless indicated otherwise, the term "wet crystalline form" refers to a polymorph that was not dried using any conventional techniques to remove residual solvent. Examples for such conventional techniques can be, but not limited to, evaporation, vacuum drying, oven drying, drying under nitrogen flow etc.

As used herein, and unless indicated otherwise, the term "dry crystalline form" refers to a polymorph that was dried using any conventional techniques to remove residual solvent. Examples for such conventional techniques can be, but not limited to, evaporation, vacuum drying, oven drying, drying under nitrogen flow etc.

As used herein, the term "isolated" in reference to solid state forms of Ixazomib Citrate of the present disclosure corresponds to a solid state form of Ixazomib Citrate that is physically separated from the reaction mixture in which it is formed.

As used herein, unless stated otherwise, the XRPD measurements are taken using copper Kα radiation wavelength 1.5418 Å.

A thing, e.g., a reaction mixture, may be characterized herein as being at, or allowed to come to "room temperature" or "ambient temperature", often abbreviated as "RT." This means that the temperature of the thing is close to, or the same as, that of the space, e.g., the room or fume hood, in which the thing is located. Typically, room temperature is from about 20° C. to about 30° C., or about 22° C. to about 27° C., or about 25° C.

The amount of solvent employed in a chemical process, e.g., a reaction or crystallization, may be referred to herein as a number of "volumes" or "vol" or "V." For example, a material may be referred to as being suspended in 10 volumes (or 10 vol or 10V) of a solvent. In this context, this expression would be understood to mean milliliters of the solvent per gram of the material being suspended, such that suspending a 5 grams of a material in 10 volumes of a solvent means that the solvent is used in an amount of 10 milliliters of the solvent per gram of the material that is being suspended or, in this example, 50 mL of the solvent. In another context, the term "v/v" may be used to indicate the number of volumes of a solvent that are added to a liquid mixture based on the volume of that mixture. For example, adding solvent X (1.5 v/v) to a 100 ml reaction mixture would indicate that 150 mL of solvent X was added.

A process or step may be referred to herein as being carried out "overnight." This refers to a time interval, e.g., for the process or step, that spans the time during the night, when that process or step may not be actively observed. This time interval is from about 8 to about 20 hours, or about 10-18 hours, typically about 16 hours.

As used herein, the term "reduced pressure" refers to a pressure that is less than atmospheric pressure. For example, reduced pressure is about 10 mbar to about 200 mbar.

As used herein and unless indicated otherwise, the term "ambient conditions" refer to atmospheric pressure, 22-24° C.

As used herein the term "low levels of residual solvents" refers to levels which are lower than the levels specified in the ICH (INTERNATIONAL COUNCIL FOR HARMONISATION OF TECHNICAL REQUIREMENTS FOR PHARMACEUTICALS FOR HUMAN USE) guidelines published for example in http://www.ich.org/fileadmin/Public_Web_Site/ICH_Products/Guidelines/Quality/Q3C/Q3C_R6_Step_4.pdf. Examples of such solvents include but are not limited to acetone, ethyl acetate, THF, acetonitrile, methyl isobutyl ketone MIBK, 2-MeTHF, n-heptane, n-butyl acetate and combinations thereof.

As used herein, crystalline forms 1 and 2 of Ixazomib Citrate refer to forms 1 and 2 as described in U.S. Pat. No. 8,859,504.

The present disclosure comprises a crystalline form of Ixazomib Citrate, designated form G. The crystalline form G of Ixazomib Citrate may be characterized by data selected from one or more of the following: an X-ray powder diffraction pattern substantially as depicted in FIG. 1; an X-ray powder diffraction pattern having peaks at 6.5, 9.9, 10.5, 16.0 and 16.2 degrees 2-theta±0.2 degrees 2-theta; and combinations of these data.

Crystalline form G of Ixazomib Citrate may be further characterized by an X-ray powder diffraction pattern having peaks as described above and also having any one, two, three, four or five additional peaks selected from the group consisting of 11.0, 13.0, 14.7, 19.3 and 21.0 degrees 2-theta±0.2 degrees 2-theta.

Figure 1:
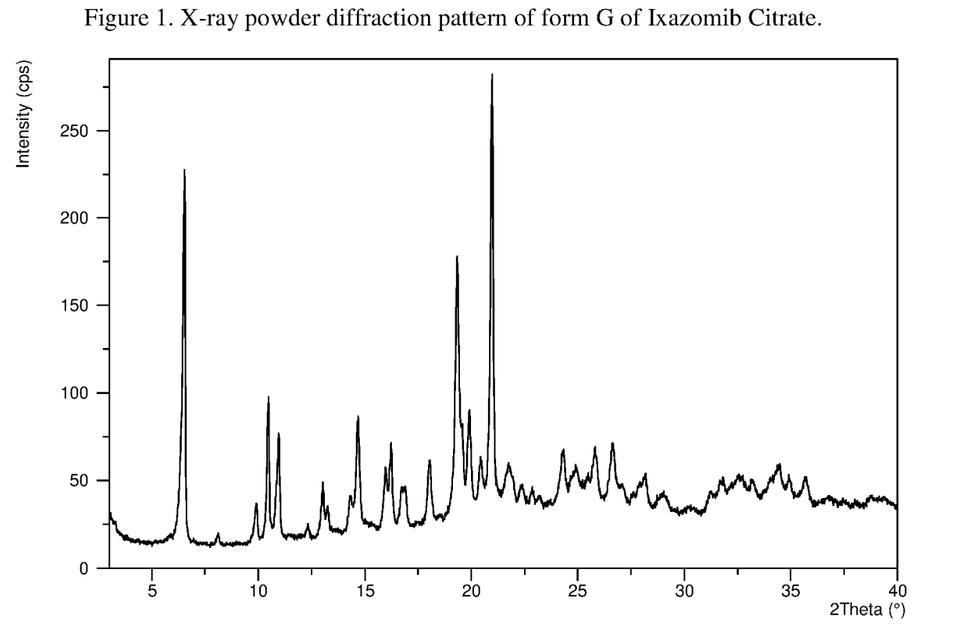
FIG. 1 shows a characteristic X-ray powder diffraction pattern of form G of Ixazomib Citrate.

Crystalline form G of Ixazomib Citrate may be characterized by each of the above characteristics alone/or by all possible combinations, e.g., an XRPD pattern having peaks at 6.5, 9.9, 10.5, 16.0 and 16.2 degrees 2-theta±0.2 degrees 2-theta; an XRPD pattern as depicted in FIG. 1, and combinations thereof.

In one embodiment of the present disclosure, form G of Ixazomib Citrate is isolated.

In another aspect, the present disclosure relates to a crystalline form of Ixazomib Citrate, designated form A. The crystalline form A of Ixazomib Citrate may be characterized by data selected from one or more of the following: an X-ray powder diffraction pattern substantially as depicted in FIG. 2; an X-ray powder diffraction pattern having peaks at 5.5, 11.0, 12.2, 12.5 and 18.8 degrees 2-theta±0.2 degrees 2-theta, and combinations of these data.

Crystalline form A of Ixazomib Citrate may be further characterized by an X-ray powder diffraction pattern having peaks as described above and also having any one, two, three, four or five additional peaks selected from the group consisting of 17.3, 19.1, 19.6, 22.7 and 25.2 degrees 2-theta±0.2 degrees 2-theta.

Figure 2:
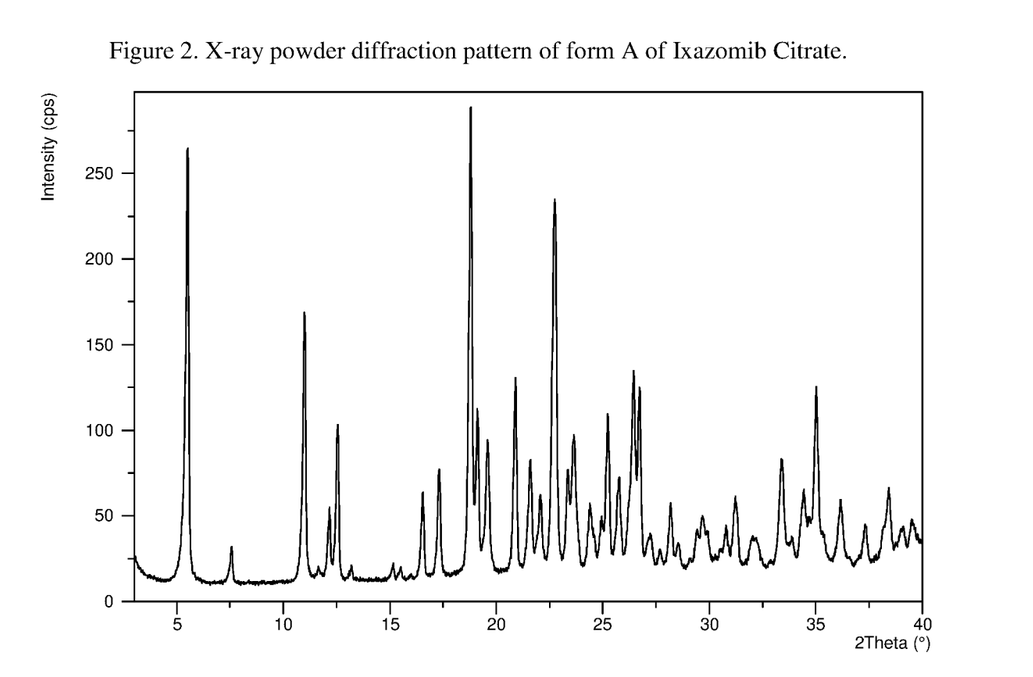
FIG. 2 shows a characteristic X-ray powder diffraction pattern of form A of Ixazomib Citrate.

Crystalline form A of Ixazomib Citrate may be characterized by each of the above characteristics alone/or by all possible combinations, e.g., an XRPD pattern having peaks at 5.5, 11.0, 12.2, 12.5 and 18.8 degrees 2-theta±0.2 degrees 2-theta; an XRPD pattern as depicted in FIG. 2, and combinations thereof.

In one embodiment of the present disclosure, form A of Ixazomib Citrate is isolated.

In another aspect, the present disclosure relates to a crystalline form of Ixazomib Citrate, designated form 1A. The crystalline form 1A of Ixazomib Citrate may be characterized by data selected from one or more of the following: an X-ray powder diffraction pattern substantially as depicted in FIG. 3; an X-ray powder diffraction pattern having peaks at 12.6, 12.9, 14.8, 15.3 and 16.4 degrees 2-theta±0.2 degrees 2-theta, and combinations of these data.

Crystalline form 1A of Ixazomib Citrate may be further characterized by an X-ray powder diffraction pattern having peaks as described above and also having any one, two, three, four or five additional peaks selected from the group consisting of 6.3, 8.2, 10.5, 19.1 and 21.1 degrees 2-theta±0.2 degrees 2-theta.

Figure 3:
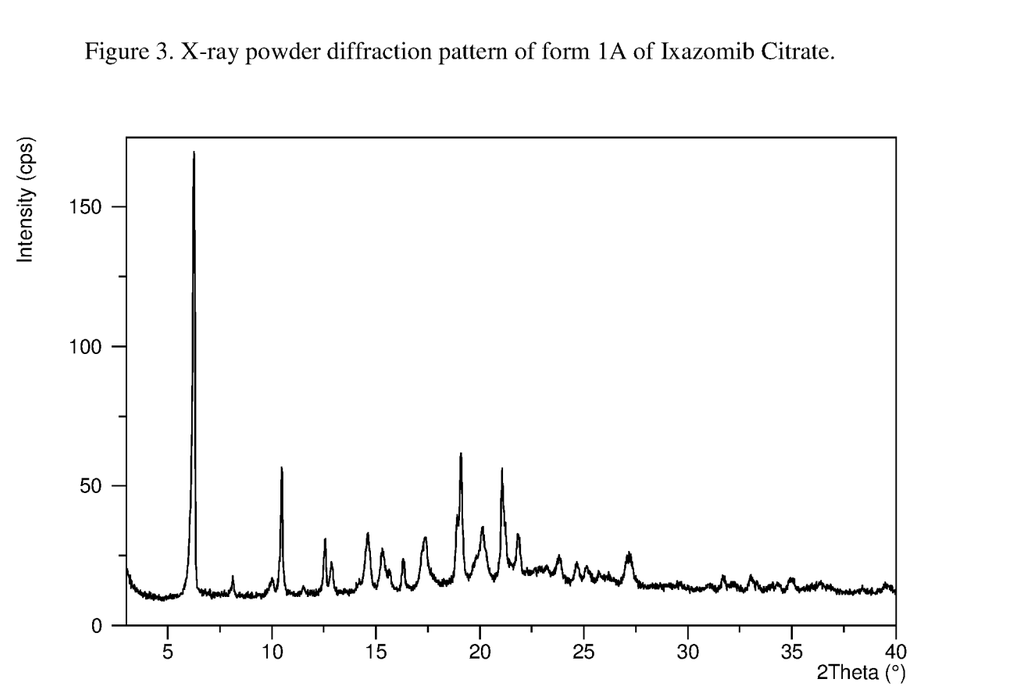
FIG. 3 shows a characteristic X-ray powder diffraction pattern of form 1A of Ixazomib Citrate.

Crystalline form 1A of Ixazomib Citrate may be characterized by each of the above characteristics alone/or by all possible combinations, e.g., an XRPD pattern having peaks at 12.6, 12.9, 14.8, 15.3 and 16.4 degrees 2-theta±0.2 degrees 2-theta; an XRPD pattern as depicted in FIG. 3, and combinations thereof.

In one embodiment of the present disclosure, form 1A of Ixazomib Citrate is isolated.

In another aspect, the present disclosure relates to a crystalline form of Ixazomib Citrate, designated form 1B. The crystalline form 1B of Ixazomib Citrate may be characterized by data selected from one or more of the following: an X-ray powder diffraction pattern substantially as depicted in FIG. 4; an X-ray powder diffraction pattern having peaks at 10.2, 10.4, 10.6, 13.3, 14.8 and 15.2 degrees 2-theta±0.2 degrees 2-theta, and combinations of these data.

Crystalline form 1B of Ixazomib Citrate may be further characterized by an X-ray powder diffraction pattern having peaks as described above and also having any one, two, three, four or five additional peaks selected from the group consisting of 6.3, 8.1, 12.6, 17.9 and 19.0 degrees 2-theta±0.2 degrees 2-theta.

Figure 4:
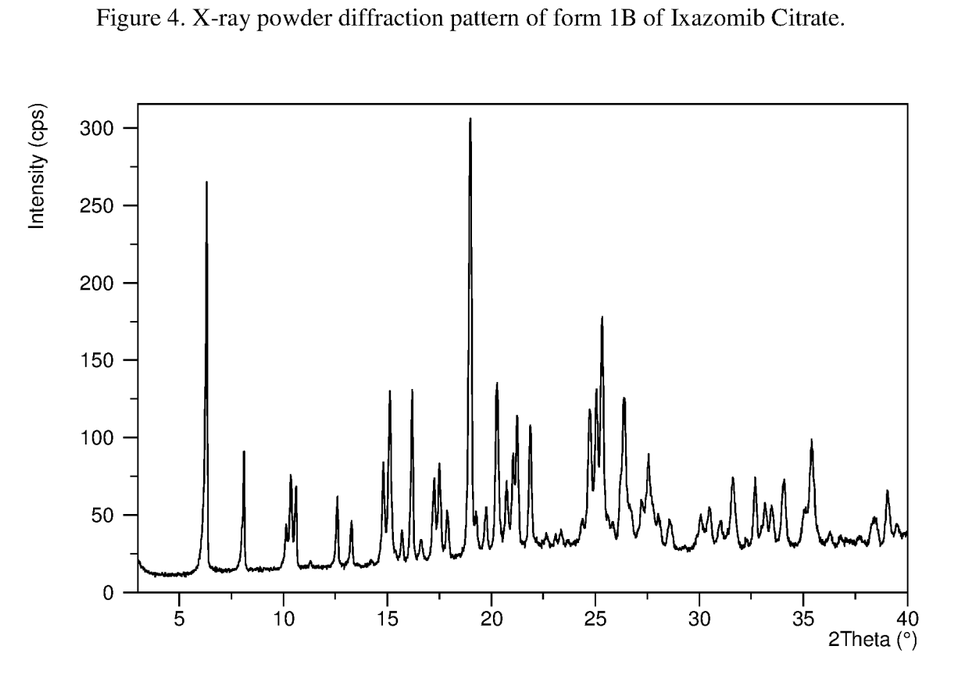
FIG. 4 shows a characteristic X-ray powder diffraction pattern of form 1B of Ixazomib Citrate.

Crystalline form 1B of Ixazomib Citrate may be characterized by each of the above characteristics alone/or by all possible combinations, e.g., an XRPD pattern having peaks at 10.2, 10.4, 10.6, 13.3, 14.8 and 15.2 degrees 2-theta±0.2 degrees 2-theta; an XRPD pattern as depicted in FIG. 4, and combinations thereof.

In one embodiment of the present disclosure, form 1B of Ixazomib Citrate is isolated.

In another aspect, the present disclosure relates to a crystalline form of Ixazomib Citrate, designated form F. The crystalline form F of Ixazomib Citrate may be characterized by data selected from one or more of the following: an X-ray powder diffraction pattern substantially as depicted in FIG. 5; an X-ray powder diffraction pattern having peaks at 6.3, 7.8, 13.2, 14.1 and 17.2 degrees 2-theta±0.2 degrees 2-theta, and combinations of these data.

Crystalline form F of Ixazomib Citrate may be further characterized by an X-ray powder diffraction pattern having peaks as described above and also having any one, two, three, four or five additional peaks selected from the group consisting of 10.0, 11.3, 14.8, 15.5 and 21.3 degrees 2-theta±0.2 degrees 2-theta.

Figure 5:
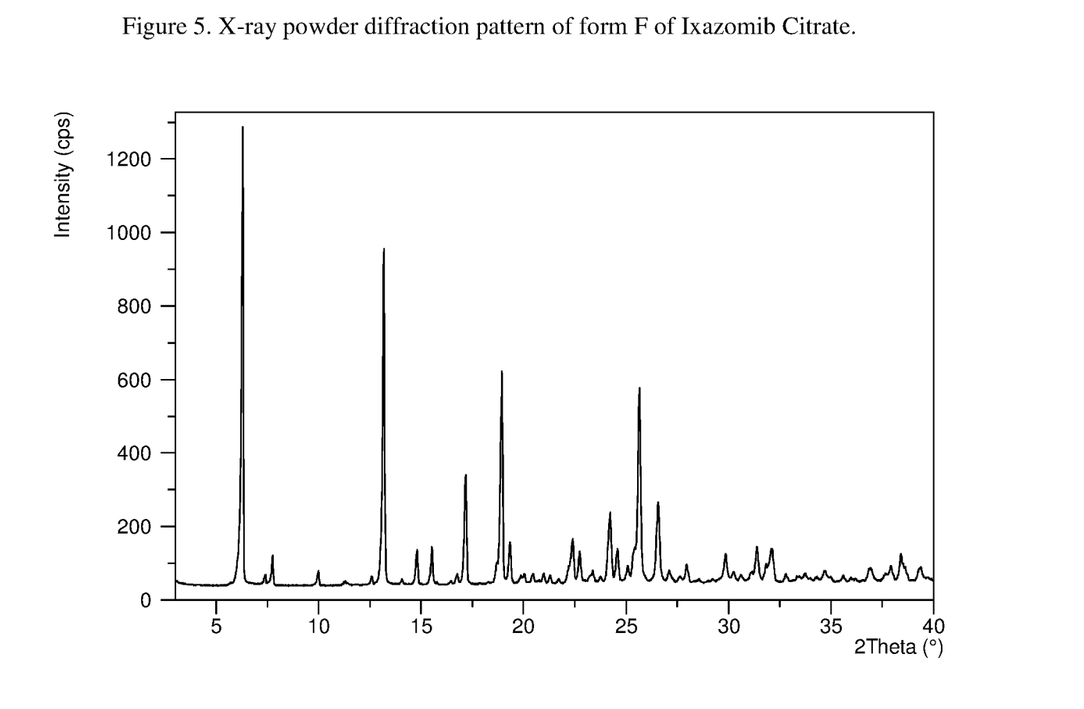
FIG. 5 shows a characteristic X-ray powder diffraction pattern of form F of Ixazomib Citrate.

Crystalline form F of Ixazomib Citrate may be characterized by each of the above characteristics alone/or by all possible combinations, e.g., an XRPD pattern having peaks at 6.3, 7.8, 13.2, 14.1 and 17.2 degrees 2-theta±0.2 degrees 2-theta; an XRPD pattern as depicted in FIG. 5, and combinations thereof.

In one embodiment of the present disclosure, form F of Ixazomib Citrate is isolated.

In a particular embodiment of the present disclosure, form F of Ixazomib Citrate is substantially free of any other form of Ixazomib Citrate, or of specified polymorphic forms of Ixazomib Citrate.

In another aspect, the present disclosure relates to a process for preparation of Ixazomib Citrate comprising a) providing of citric acid, a suitable ketone, optionally one or more solvents and compound 2:

Compound 2

Wherein R1 and R2, taken together with the intervening oxygen and boron atoms, form an optionally substituted 5- to 10-membered ring having 0-2 additional ring heteroatoms selected from N, O, or S, preferably R1 and R2, taken together with the intervening oxygen and boron atoms, form an optionally substituted 5 or 6 membered ring, In specific embodiments, R1 and R2 together form a chiral moiety.

More preferably compound of formula 2 is—

Wherein R3 and R6 are each independently selected from the group consisting of hydrogen and C1-C5 alkyl; R4 and R5 taken together form an optionally substituted C5 to C7 carbocycle, wherein the total number of carbon atoms is not more than 10.

Most preferably, compound 2 is: 2,5-Dichloro-N-[2-[[(1R)-1-[(3aS,4S,6S,7aR)-hexahydro-3a,5,5-trimethyl-4,6-methano-1,3,2-benzodioxaborol-2-yl]-3-methylbutyl]amino]-2-oxoethyl]benzamide;

b) adding a strong acid, preferably HCl, to afford Ixazomib Citrate; and c) optionally isolating Ixazomib Citrate; and Wherein the reaction is performed in the absence of an organic boronic acid or boric acid acceptor.

Suitable ketones may include, but are not limited to, C3-C9 ketones, preferably C3-C6 ketones, such as acetone or MIBK; more preferably, the ketone is acetone.

In one embodiment, the reaction is performed in a ketone solvent, preferably acetone as a single solvent.

The step of isolating Ixazomib Citrate may be performed by crystallization.

The above described processes may be a one pot process.

The above described processes may be performed in a one phase system.

The above described processes may be performed in the absence of an organic boronic acid or boric acid acceptor In one embodiment, the amount of HCl in step b is a catalytic amount, i.e. less than an equimolar amount. Preferably the amount required is about 50 mol % or less, about 30 mol % or less, about 20 mol % or less, about 10 mol % or less, about 5 mol % or with respect to the amount of starting material compound 2, preferably 2,5-Dichloro-N-[2-[[(1R)-1-[(3aS,4S,6S,7aR)-hexahydro-3a,5,5-trimethyl-4,6-methano-1,3,2-benzodioxaborol-2-yl]-3-methylbutyl]amino]-2-oxoethyl]benzamide.

In some embodiments, steps a) and b) may be interchangeable or all the components provided in step a) and b) may be provided together.

The reaction may typically be performed at elevated temperature (up to reflux temperature) under stirring, for about 1 to about 5 hours. When the ketone is acetone the steps a) and b) may be performed at about 40 to about 55° C.

In a preferred aspect the present disclosure relates to a process for preparation of Ixazomib Citrate comprising a)

providing a mixture of 2,5-Dichloro-N-[2-[[(1R)-1-[(3aS, 4S,6S,7aR)-hexahydro-3a,5,5-trimethyl-4,6-methano-1,3,2-benzodioxaborol-2-yl]-3-methylbutyl]amino]-2-oxoethyl] benzamide, citric acid and a suitable ketone and optionally one or more solvents; b) adding a strong acid, preferably HCl, to afford Ixazomib Citrate; and c) optionally isolating Ixazomib Citrate, wherein the reaction is performed in the absence of an organic boronic acid or boric acid acceptor.

In another aspect the present disclosure relates to a process for preparation of Ixazomib Citrate comprising deprotection of 2,5-Dichloro-N-[2-[[(1R)-1-[(3aS,4S,6S, 7aR)-hexahydro-3a,5,5-trimethyl-4,6-methano-1,3,2-benzodioxaborol-2-yl]-3-methylbutyl]amino]-2-oxoethyl]benzamide in a one phase system, comprising a ketone, and optionally one or more solvents, in the absence of a boronic acid or boric acid acceptor.

The process is performed in the presence of an inorganic acid.

The one phase system may comprise of a ketone and optionally one or more solvents. Suitable lower ketones may include, but are not limited to C3-C9 ketones preferably C3-C6 ketones such as acetone or MIBK; more preferably, the ketone is acetone.

In one embodiment, the reaction is performed in a ketone solvent, preferably acetone as a single solvent.

In one embodiment, the deprotection step comprises use of HCl in catalytic amounts.

The deprotection step may be accomplished by formation of pinanediol ketals, preferably acetone ketals (i.e. acetonide of pinanediol). Ketals may include, but are not limited to, C3-C9 ketals, preferably C3-C6 ketals such as acetone or MIBK ketals; more preferably, the ketal is an acetone ketal.

The deprotection step may preferably be carried out in the absence of an organic boronic acid or boric acid acceptor.

In another aspect, the present disclosure provides processes for preparation of Ixazomib citrate, preferably form 2 of Ixazomib citrate, more preferably form 2 that is substantially free of form 1 of Ixazomib Citrate, having low levels of residual solvents, as described above, comprising A) providing crystalline form F of Ixazomib Citrate and B) converting crystalline form F of Ixazomib Citrate to Ixazomib Citrate having low levels of residual solvents.

Form F may be converted to Ixazomib Citrate having low levels of residual solvents for example by drying or by slurrying Ixazomib citrate form F in a solvent or mixture of solvents that form F is not soluble in, such as n-heptane, at an elevated temperature.

Preferably Ixazomib Citrate formed in step B is form 2, more preferably form 2 that is substantially free of any other form of Ixazomib Citrate of Ixazomib Citrate.

Preferably crystalline form F is converted to form 2, more preferably form 2 that is substantially free of form 1 of Ixazomib Citrate, by drying of form F for a sufficient time under appropriate conditions to afford crystalline form 2. Preferably the drying is performed at a temperature of about 40 to about 60° C. and a pressure of about 50 mbar to about 300 mbar. Most preferably, the above process comprises a step of filtering the reaction mixture and drying preferably below 100 mbar and at a temperature of about 50 to about 60° C. to afford form 2 of Ixazomib Citrate.

The present disclosure provides processes for preparation of form F of Ixazomib Citrate.

Preferably, form F used in step A is that is substantially free of any other form of Ixazomib citrate Form F may be prepared as according to the following processes.

In a preferred embodiment, the disclosure provides a process for preparation of Ixazomib Citrate form F, preferably substantially free of any other forms, comprising the following steps:

i) providing 2,5-Dichloro-N-[2-[[(1R)-1-[(3aS,4S,6S, 7aR)-hexahydro-3a,5,5-trimethyl-4,6-methano-1,3,2-benzodioxaborol-2-yl]-3-methylbutyl]amino]-2-oxoethyl]benzamide, citric acid, acetone and HCl; ii) optionally concentrating the reaction mixture iii) optionally seeding with Ixazomib citrate form 2; iv) optionally diluting and/or optionally stirring; and v) optionally cooling and keeping at low temperature until crystallization is complete.

Preferably, in step i) the amount of HCl may be less than equimolar amount, preferably, less than about 50 mol %, less than about 30 mol %, less than about 20 mol %, less than about 10 mol %, less than about 5 mol % with respect to the starting material, 2,5-Dichloro-N-[2-[[(1R)-1-[(3 aS,4S,6S, 7aR)-hexahydro-3a,5,5-trimethyl-4,6-methano-1,3,2-benzodioxaborol-2-yl]-3-methylbutyl]amino]-2-oxoethyl]benzamide.

In step ii) the reaction mixture may be concentrated to a volume of about 7 to about 20 V.

In step iv) the dilution solvent is preferably acetone. The reaction mixture may be stirred for about 1 to about 4 hours at a temperature of about 40 to about 55° C.

In step v) the reaction mixture may be cooled to a temperature of about (−20) to about 15° C., preferably the reaction may be cooled to a temperature of about (−5) to about 5° C. The reaction may be kept at this temperature over-night.

In a further preferred embodiment the disclosure provides another process for preparation of Ixazomib Citrate form F, preferably substantially free of any other forms, comprising the following steps:

a) providing Ixazomib Citrate in THF b) warming the mixture to a temperature of about 40 to about 60° C. and stirring until dissolution c) concentrating the mixture under vacuum to minimal volume; d) dissolving the residue in acetone; e) optionally seeding with crystalline Ixazomib Citrate or stirring until spontaneous crystallization occurs;

Preferably, form 2 produced by the process is substantially free of form 1.

Particularly, crystalline form 2 of Ixazomib Citrate produced by the process of the present invention contains: less than 10 wt %, less than 5 wt %, less than 2 wt %, less than 1 wt %, of crystalline Form 1 of Ixazomib Citrate, as measured by XRPD. Accordingly, the content of crystalline Ixazomib Citrate form 1 in crystalline Ixazomib Citrate form 2 will be measured by detecting and quantifying the described characteristic peaks of form 1. The characteristic peaks of crystalline Ixazomib Citrate form 1 used for the above described measurement can be any one of peaks at: 6.3, 8.1, 10.2 and 19.0 degrees two theta±0.2 degrees two theta.

Crystalline form 1 of Ixazomib Citrate produced according to the present disclosure contains: less than 10 wt %, less than 5 wt %, less than 2 wt %, less than 1 wt %, of crystalline Form 2 of Ixazomib Citrate, as measured by XRPD. Accordingly, the content of crystalline Ixazomib Citrate form 2 in crystalline Ixazomib Citrate form 1 will be measured by detecting and quantifying the described characteristic peaks of form 2. The characteristic peaks of crystalline Ixazomib Citrate form 2 used for the above described measurement can be any one of peaks at: 5.7, 7.5, 11.5, 11.8 or 16.6 degrees two theta±0.2 degrees two theta.

In a further aspect, the disclosure provides Crystalline Form 2 of Ixazomib citrate, which is substantially free of form 1 of Ixazomib citrate, and having low levels of residual solvents, as defined above.

In a further aspect, the disclosure provides Crystalline Form 1 of Ixazomib citrate, which is substantially free of form 2 of Ixazomib citrate, and having low levels of residual solvents, as defined above.

In another preferred embodiment, the disclosure provides a further process for preparation of Ixazomib Citrate form 2, preferably substantially free of form 1 and having low levels of residual solvents as described above comprising the following steps:

a) providing Ixazomib Citrate in THF b) warming the mixture to a temperature of about 40 to about 60° C. and stirring until dissolution c) concentrating the mixture under vacuum to minimal; d) dissolving the residue in acetone; e) optionally seeding with crystalline Ixazomib Citrate (form 1, form F of form 2 or mixture thereof); f) cooling to a temperature of about (−20) to about 5° C.; g) warming to a temperature of about 40 to about 55° C. and cooling back to a temperature of about (−20) to about 5° C.; h) warming to a temperature of about 40 to about 55° C. and treating at about 40 to about 55° C. for about 1 to about 2 hours; i) cooling back to a temperature of about (−20) to about 5° C. and optionally keeping the reaction mixture at the same temperature until completion of crystallization; and j) filtering the mixture and drying to afford form 2 of Ixazomib citrate.

In step c) the concentration step may be performed at a temperature of about 30 to about 45° C.

In step e) seeding may be performed at a temperature of about 10 to about 20° C.

In each one of steps f), g), h) and i) the cooling or heating may be performed about 10 minutes to about 1 hour.

In step i) the crystallization will typically be completed within about 10 hours.

In step j) drying may be performed under vacuum, preferably below 100 mbar and at a temperature of about 50 to about 60° C.

The above solid state forms can be used to prepare other solid state forms of Ixazomib Citrate, Ixazomib Citrate salts, and solid state forms thereof.

Specifically, form F of Ixazomib citrate, preferably form F that is substantially free of any other form of Ixazomib Citrate, may be used for preparing Ixazomib Citrate, preferably crystalline form 2, more preferably form 2 that is substantially free of form 1 of Ixazomib Citrate, having low levels of residual solvents. Examples of such solvents include but are not limited to acetone, ethyl acetate, THF, acetonitrile, MIBK, 2-MeTHF, n-heptane, n-butyl acetate and combinations thereof.

For example, form F, preferably form F that is substantially free of any other form of Ixazomib citrate, may be used for preparation of Ixazomib Citrate, preferably form 2, more preferably form 2 that is substantially free form 1 of Ixazomib Citrate having less than about 5000 ppm of acetone, preferably containing about 40 to about 4000 ppm of acetone, more preferably containing 40 to about 3000 of acetone, most preferably containing 40-2000 ppm of acetone.

For Example, form F, preferably form F that is substantially free of any other form of Ixazomib Citrate, may be used for preparation of Ixazomib Citrate, preferably form 2 more preferably form 2 that is substantially free of form 1 of Ixazomib Citrate having less than about 5000 ppm of ethyl acetate, preferably less than about 3000 ppm of ethyl acetate, more preferably less than about 1000 ppm of ethyl acetate, most preferably less than about 100 ppm of ethyl acetate.

For Example, Form F, preferably form F that is substantially free of any other form of Ixazomib Citrate, may be used for preparation of Ixazomib citrate, preferably form 2 more preferably form 2 that is substantially free of form 1 of Ixazomib Citrate having less than about 720 ppm of THF, preferably containing about 30 to about 720 ppm of THF, more preferably containing about 30 ppm to about 500 ppm of THF, most preferably containing about 30 ppm to about 200 ppm of THF.

Form F, preferably form F that is substantially free of any other form of Ixazomib Citrate, may be used for preparation of Ixazomib citrate as exemplified in any of the above non-limiting examples or combinations thereof.

In another aspect, the disclosure provides form F of Ixazomib citrate, preferably form F that is substantially free of any other form of Ixazomib Citrate, for use in the preparation of Ixazomib citrate, preferably crystalline form 2, more preferably form 2 that is substantially free of form 1 of Ixazomib Citrate, having low levels of residual solvents, as exemplified in any of the above non-limiting examples or combinations thereof.

In a further aspect, the disclosure provides Ixazomib citrate having low levels of residual solvents produced by the processes of the disclosure.

The present disclosure provides solid state forms of Ixazomib Citrate for use in the preparation of pharmaceutical compositions comprising Ixazomib Citrate.

The present disclosure also encompasses the use of the Ixazomib Citrate solid state forms of the present disclosure for the preparation of pharmaceutical compositions of Ixazomib Citrate.

The present disclosure comprises processes for preparing the above mentioned pharmaceutical compositions. The processes comprise combining the Ixazomib Citrate solid state forms with at least one pharmaceutically acceptable excipient.

The solid state forms and the pharmaceutical compositions of Ixazomib Citrate of the present disclosure can be used as medicaments, particularly for the treatment of multiple myeloma.

The present disclosure also provides methods of treating multiple myeloma comprising administering a therapeutically effective amount of a Ixazomib Citrate solid state form of the present disclosure, or at least one of the above pharmaceutical compositions, to a subject in need of the treatment.

Having thus described the disclosure with reference to particular preferred embodiments and illustrative examples, those in the art can appreciate modifications to the disclosure as described and illustrated that do not depart from the spirit and scope of the disclosure as disclosed in the specification. The Examples are set forth to aid in understanding the disclosure but are not intended to, and should not be construed to limit its scope in any way.

Powder X-ray Diffraction ("PXRD") Method

Powder X-ray Diffraction was performed on an X-Ray powder diffractometer PanAlytical X'pert Pro; CuKα radiation (X=1.541874 Å); X'Celerator detector with active length 2.122 degrees 2-theta; laboratory temperature 25±3° C.; zero background sample holders. Prior to analysis, the samples were gently ground using a mortar and pestle to obtain a fine powder. The ground sample was adjusted into a cavity of the sample holder and the surface of the sample was smoothed using a cover glass.

Measurement parameters:

| | |
|---|---|
| Scan range | 3-40 degrees 2-theta |
| Scan mode | continuous |
| Step size | 0.0167 degrees |
| Step size | 42 s |
| Sample spin | 60 rpm |
| Sample holder | zero background silicon plate |

Method for Determination of Residual Solvents

Residual solvents content was determined by gas chromatography using Agilent 7890 gas chromatograph with FID detector and headspace sampler Agilent 7697. The gas chromatograph was equipped with a column Agilent RES-SOLV, Part No. 19095V-420, 30 m×0.53 mm i.d.×1 μm, the oven was heated at 40° C. for 4.2 minutes and then was the temperature increased onto 200° C. at rate of 25° C./min and the constant flow of carrier-gas (He) was 4.8 mL/min. The headspace vials were equilibrated at 90° C. for 20 minutes. Split was 1:6. Samples were prepared by weighing exactly about 50.0 mg of the solid sample into a 20-mL headspace vial, exactly 0.50 mL of DMSO was added by a gas tight syringe and the vial was sealed immediately. After temperature incubation and equilibration, 1.0 mL of gaseous phase was injected for analysis.

The analyte peaks in the sample solution were identified based on comparison of the retention times with the average retention times of the analytes in calibration solutions. Content of analytes were determined using the method of external standard.

EXAMPLES

WO 2009/154737 describes a process of obtaining form 1 and form 2 of Ixazomib Citrate.

Example 1. Preparation of Form G of Ixazomib Citrate

A. Procedure 1

Ixazomib Citrate (form 2, 1 g) was suspended in ethanol (14.4 ml) and heated up to 70° C. during 30 min. After dissolution of the crystalline material, the solution was cooled down to 20° C. during 30 min. At this temperature, the solution was seeded with Ixazomib Citrate form 2 (16 mg); after seeding, the suspension was stirred at this temperature for 30 min. and then cooled down to 0° C. during 1 hour. At this temperature n-heptane (8 ml) was added and the suspension was stirred for 3 hours. After this time the crystal was filtered off, washed with n-heptane (1 ml) and dried at 45° C. for 5 hours under a stream of nitrogen to provide Form G (as confirmed by XRPD).

B. Procedure 2

Ixazomib Citrate (form 2, 1 g) was suspended in n-propanol (15.0 ml) and heated up to 90° C. during 30 min. After dissolution of the crystalline material, the solution was cooled down to 25° C. during 30 min. At this temperature, the solution was given to evaporator and concentrated to 27% of the original weight. Then the solution was cooled down from 25° C. to 0° C. during 1 hour. The crystallization is completed in the end of the cooling. While keeping the suspension at 0° C., n-heptane (8 ml) was added and the suspension was stirred for 2 hours. Then the crystal was filtered off, washed with n-heptane (1 ml) and dried at 45° C. for 5 hours under a stream of nitrogen. Polymorphic form G was confirmed by PXRD analysis. The product was analyzed by XRPD, indicating that form G was obtained. The XRPD pattern is presented in FIG. 1.

Example 2. Preparation of Form A of Ixazomib Citrate 2,5-Dichloro-N-[2-[[(1R)-1-[(3aS,4S,6S,7aR)-hexahydro-3a,5,5-trimethyl-4,6-methano-1,3,2-benzodioxaborol-2-yl]-3-methylbutyl]amino]-2-oxoethyl]benzamide (206 g) and citric acid hydrate (113.6 g) were dissolved in acetone (2060 mL). To obtained solution, concentrated aqueous HCl (5.2 mL) was added. The reaction mixture was warmed to about 50° C. After about 3.5 h of stirring at 45-54° C., the reaction mixture concentrated under reduced pressure (30-50 kPa, process temperature 25-35° C., internal temperature about 45° C.) to about half of the original volume. Concentrated solution was diluted with ethyl acetate (1030 mL) and subsequently concentrated under reduced pressure (30-50 kPa, process temperature 25-35° C., internal temperature about 45° C.) to about 1 L (crystallization started during the concentration). Obtained mixture was again diluted with ethyl acetate (1030 mL) and concentrated under reduced pressure (30-50 kPa, process temperature 25-35° C., internal temperature about 45° C.) to about 1 L. The mixture was diluted with ethyl acetate (1525 mL) and concentrated under reduced pressure (30-50 kPa, process temperature 25-35° C., internal temperature about 45° C.) to about 2.4 L. The mixture was warmed to about 50° C. After about 2 h of stirring at about 50° C., the mixture was cooled during about 1.5 h to about 25° C. and then stirred at about 25° C. for additional 1.5 h. Insoluble solid was separated by filtration, washed with ethyl acetate (3×515 mL) and dried in vacuum oven (about 100 mbars, about 50° C.) for 6 hours to provide 215 g of Ixazomib Citrate Form A. The product was analyzed by XRPD, indicating that form A was obtained. The XRPD pattern is presented in FIG. 2. Residual solvents: ethyl acetate 8900 ppm, acetone 6057 ppm Example 3. Preparation of Form 1A of Ixazomib Citrate Ixazomib citrate form G was placed into TGA pan and the pan was heated to 180° C. in TGA furnace by heating rate 10° C./min under nitrogen flow (50 mL/min). The pan was unloaded from the TGA furnace to allow the sample to cool down to ambient temperature. The obtained product was analyzed by XRPD, indicating that form 1A was obtained. The XRPD pattern is presented in FIG. 3.

Example 4. Preparation of Form 1B of Ixazomib Citrate

Ixazomib citrate form 1 (about 1 g) was placed in a Petri dish and was exposed to 80% relative humidity at temperature 25° C.+2° C. for a period of 4 days.

The obtained product was analyzed by XRPD, indicating that form 1B was obtained. The XRPD pattern is presented in FIG. 4.

Figure 6:
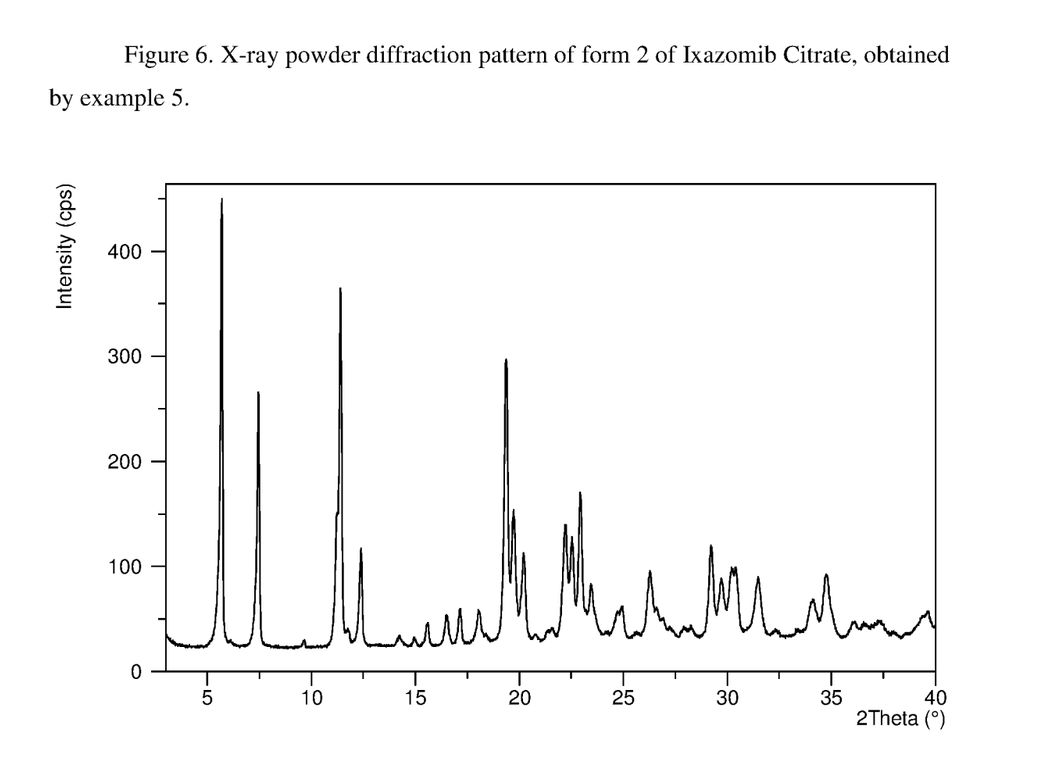
FIG. 6 shows the X-ray powder diffraction pattern of form 2 of Ixazomib Citrate, obtained by example 5.

Example 5. Preparation of Form 2 of Ixazomib Citrate Having Low Levels of Residual Solvents A double jacket glass reactor was charged with Ixazomib citrate form 2 (100 g, 727 ppm of acetone, 1% of ethyl acetate, obtained by example 6) and tetrahydrofuran (2.2 L). Obtained suspension was warmed to about 60° C. and stirred at this temperature until dissolution. The solution was concentrated under reduce pressure (about 500 mbars) to minimal volume at 30-45° C. (jacket temperature was about 55° C.). Obtained viscous non-crystalline compound was dissolved in acetone (2.0 L) at temperature about 20° C. The solution was seeded with Ixazomib citrate Form 1 (3.0 g) and the mixture was stirred about 20 minutes at about 20° C. The mixture was cooled during about 1 hour to 0° C. and then it was warmed during about 1 hour to about 50° C. After about 1 hour treatment at about 50° C., the mixture was cooled during about 1 hour back to about 0° C. and it was treated at about 0° C. for about 15 minutes. The mixture was again warmed during about 1 h to about 50° C. and treated at about 50° C. for additional 1 h. The mixture was finally cooled during about 1 hour back to about 0° C. and it was treated at about 0° C. for about 13 hours. Insoluble solid was separated by filtration and washed with cold (0-5° C.) acetone (500 mL). The obtained product (91 g) was analyzed by XRPD analysis and identified as by Ixazomib citrate Form F. The XRPD pattern is presented in FIG. 5. The obtained Ixazomib citrate Form F was dried in vacuum oven at temperature about 60° C. and pressure about 200 mbars, which provided transformation to Ixazomib citrate Form 2, free of form 1 (83 g, 2967 ppm of residual acetone and 130 ppm of residual tetrahydrofuran), as identified by XRPD and the XRPD pattern is presented in FIG. 6.

Example 6. Preparation of Form 2 of Ixazomib Citrate Having High Levels of Residual Solvents A double jacket glass reactor was charged with 2,5-dichloro-N-[2-[[(1R)-1-[(3aS,4S,6S,7aR)-hexahydro-3a,5,5-trimethyl-4,6-methano-1,3,2-benzodioxaborol-2-yl]-3-methylbutyl]amino]-2-oxoethyl]benzamide (2000 g), citric acid monohydrate (1103 g), conc. aqueous HCl (51 mL) and acetone (20 L). Obtained solution was warmed to about 45° C. and stirred at 45-50° C. for about 4.5 hours. The solution was concentrated under reduced pressure (about 30 kPa, process temperature 25-40° C., internal temperature about 55° C.) to about one third of the original volume (about 7 L) and the residue was diluted with ethyl acetate (10 L). Obtained mixture was concentrated to about 10 L and diluted again with ethyl acetate (10 L). Obtained mixture was concentrated to about 16 L and diluted again with ethyl acetate (14.8 L). Obtained mixture was concentrated to about 23 L and then it was warmed to 45-50° C. After about 2 hours treatment at 45-50° C., the mixture was cooled to about 25° C. during about 1.5 hour and stirred at about 25° C. for additional 1 hour. Insoluble solid was separated by filtration, washed with ethyl acetate (3×5 L) and dried in vacuum oven at temperature about 50° C. and pressure below 100 mbars to give Ixazomib citrate Form 2 (1908 g, 727 ppm of acetone, 1% of ethyl acetate), as identified by XRPD.

Example 7. Preparation of Form 2 of Ixazomib Citrate Having Low Level of Residual Solvents A double jacket glass reactor was charged with 2,5-dichloro-N-[2-[[(1R)-1-[(3aS,4S,6S,7aR)-hexahydro-3a,5,5-trimethyl-4,6-methano-1,3,2-benzodioxaborol-2-yl]-3-methylbutyl]amino]-2-oxoethyl]benzamide (2010 g), citric acid monohydrate (1109 g), conc. aqueous HCl (51 mL) and acetone (20.1 L). The obtained solution was warmed to about 45° C. and stirred at 45-50° C. for about 2 hours. The solution was seeded with suspension of Ixazomib citrate (10 g, mixture of Form F and Form 2) in acetone (100 mL). Obtained suspension was treated about 1 hour at 45-50° and then it was cooled to about 0° C. during about 2.5 hours. After additional 1 hour treatment at about 0° C., insoluble solid was separated by filtration, washed with cold (about 0° C.) acetone (3×6 L) and dried in vacuum oven at temperature about 50° C. and pressure below 100 mbars to give Ixazomib citrate Form 2 (1351 g, 1735 ppm of acetone), as identified by XRPD. Partial concentration of mother liquor and acetone washes to about 7 L and cooling to about 0° C. provided second crop of Ixazomib citrate which after isolation and drying (467 g, 1735 ppm of acetone, less than 30 ppm ethyl acetate) was identified by XRPD as Form 2, free of form 1.

Example 8. Preparation of Form 2 of Ixazomib Citrate Having Low Level of Residual Solvents A double jacket glass reactor was charged with 2,5-dichloro-N-[2-[[(1R)-1-[(3aS,4S,6S,7aR)-hexahydro-3a,5,5-trimethyl-4,6-methano-1,3,2-benzodioxaborol-2-yl]-3-methylbutyl]amino]-2-oxoethyl]benzamide (30 g), citric acid monohydrate (16.55 g), conc. aqueous HCl (0.76 mL) and acetone (300 mL). The obtained solution was warmed to about 45° C. and stirred at 45-50° C. for about 2.5 hours. The reaction mixture was concentrated under reduce pressure and temperature 30-50° C. (jacket temperature was 65° C.) to about 200 mL, which resulted to spontaneous crystallization. Ixazomib Citrate form 2 (about 20 mg) was added to obtained suspension together with acetone (30 mL). After about 45 minutes of stirring at 45-50° C., the suspension was cooled to about 0° C. during about 1.5 hours. After additional 19 hours treatment at about 0° C., insoluble solid was separated by filtration, washed with cold (about 0° C.) acetone (2×60 mL) and dried in vacuum oven at temperature 50-60° C. and pressure below 100 mbars to give Ixazomib Citrate form 2, free of form 1 (28.44 g, 1713 ppm of acetone), as identified by XRPD.

Example 9. Preparation of Form 2 of Ixazomib Citrate Having Low Level of Residual Solvents 1-[(3aS,4S,6S,7aR)-hexahydro-3a,5,5-trimethyl-4,6-methano-1,3,2-benzodioxaborol-2-yl]-3-methylbutyl] amino]-2-oxoethyl]benzamide (2512 g), citric acid monohydrate (1387 g), conc. aqueous HCl (64 mL) and acetone (25.1 L). The obtained solution was warmed to about 45° C. and stirred at 45-50° C. for about 3.5 hours. The reaction mixture was concentrated under reduce pressure and temperature 30-50° C. (jacket temperature was 65° C.) to about 17.5 L, which resulted to spontaneous crystallization Obtained suspension was diluted with acetone (2.5 L). After about 35 minutes of stirring at 45-50° C., the suspension was cooled to about 0° C. during about 1.5 hours. After additional 16 hours treatment at about 0° C., insoluble solid was separated by filtration, washed with cold (about 0° C.) acetone (2×5 L) and dried in vacuum oven at temperature 50-60° C. and pressure below 100 mbars to give Ixazomib Citrate form 2+form F (2 386 g, 3728 ppm of acetone), as identified by XRPD. Sample (about 10 g) was additionally dried in vacuum oven at temperature 50-70° C. and pressure below 100 mbars to give Ixazomib Citrate form 2, free of form 1 (1831 ppm of acetone), as identified by XRPD.

Part of obtained Ixazomib Citrate mixture of form 2+form F (2160 g) was divided to two portions (2×1080 g,). Each portion was dissolved in tetrahydrofuran (27 L) at temperature about 55° C., received solution was cooled to 35-40° C. and then filtered through filtration capsule (mesh size 0.45 micron). Filtrates from dissolution of both portions were combined and concentrated under reduced pressure (100-300 mbars) and temperature up to 40° C. (jacket temperature of used reactor was about 65° C.) to minimal volume (about 2.5 L,). Received viscous non-crystalline compound was dissolved in acetone (21 L) at temperature about 20° C. The solution was filtered through filtration capsule (mesh size 0.45 micron) and used filtration capsule was rinsed with acetone (0.5 L). Primary filtrate was combined with filtrate from the rinsing and the solution was seeded with suspension of Ixazomib Citrate form 2 (22 g, prepared according to example 10) in acetone (0.44 L) and the mixture was stirred about 20 minutes at about 20° C. The mixture was cooled during about 1 hour to about 0° C. and then it was warmed during about 1.5 hour to about 55° C. After about 1 hour treatment at about 55° C., the mixture was cooled during about 1.5 hour back to about 0° C. and it was treated at about 0° C. for about 15 minutes. The mixture was again warmed during about 1.5 hour to about 55° C. and treated at about 55° C. for additional 1 hour. The mixture was finally cooled during about 1.5 hour back to about 0° C. and it treated at about 0° C. for about 10 hours. Insoluble solid was separated by filtration, washed twice with cold (−5 0° C.) acetone (4.2 L) and dried in vacuum oven at temperature 50-60° C. and pressure below 100 mbars to give Ixazomib Citrate form 2, free of form 1 (1977 g, 1986 ppm of residual acetone and 435 ppm of residual tetrahydrofuran), as identified by XRPD.

Example 10. Preparation of Form 2 of Ixazomib Citrate Having Low Level of Residual Solvents Ixazomib Citrate form 2 (1900 g) was divided to two portions (1000+900 g,). Each portion was dissolved in tetrahydrofuran (25.0+22.5 L) at temperature about 55° C., received solution was cooled to 35-40° C. and then filtered through filtration capsule (mesh size 0.2 micron). Filtrates from dissolution of both portions were combined and concentrated under reduced pressure (about 250 mbars) and temperature up to 45° C. (jacket temperature of used reactor was about 60° C.) to minimal volume (about 2 L). Received viscous non-crystalline compound was dissolved in acetone (14 L) at ambient temperature. The solution was filtered through filtration capsule (mesh size 0.2 micron) and used filtration capsule was rinsed with acetone (about 5 L). Primary filtrate was combined with filtrate from the rinsing and the solution was seeded with suspension of Ixazomib Citrate form 1 (28 g) in acetone (0.6 L) at about 20° C. Obtained mixture was stirred about 20 minutes at 20-25° C. The mixture was cooled during about 1 hour to about 0° C. and then it was warmed during about 1.5 hour to about 55° C. After about 1 hour treatment at about 55° C., the mixture was cooled during about 1.5 hour back to about 0° C. and it was treated at about 0° C. for about 15 minutes. The mixture was again warmed during about 1.5 hour to about 55° C. and treated at about 55° C. for additional 1 hour. The mixture was finally cooled during about 1.5 hour back to about 0° C. and it treated at about 0° C. for about 11 hours. Insoluble solid was separated by filtration, washed twice with cold (−5-0° C.) acetone (3.8 L) and dried in vacuum oven at temperature 50-60° C. and pressure below 100 mbars to give Ixazomib Citrate form 2, free of form 1 (1750 g, 2032 ppm of residual acetone and 301 ppm of residual tetrahydrofuran), as identified by XRPD.

Example 11. Preparation of Form 1 of Ixazomib Citrate Having Low Level of Residual Solvents (Sonocrystallization)

Ixazomib Citrate form 2 (5 g, 727 ppm of acetone, 1% of ethyl acetate, obtained by example 6) was dissolved in tetrahydrofuran (110 mL) at temperature about 40° C. Obtained solution was concentrated under reduced on rotary evaporator (pressure about 250 mbars and bath temperature about 44° C.) to about 10.4 g. Received viscous non-crystalline compound was dissolved in ethyl acetate (100 mL) at ambient temperature. The solution was treated by ultrasound (ultrasound probe, 5 seconds pulse, 1 second pause, amplitude 30%) for about 0.5 hour and at ambient temperature, which resulted to solid compound creation. The mixture was cooled during about 2 hours to about 0° C. and it was treated at about 0° C. for about 2.5 hours. Insoluble solid was separated by filtration and dried in an oven at temperature about 60° C. to give Ixazomib Citrate form1, free of form 2 (230 ppm of residual ethyl acetate and 141 ppm of residual tetrahydrofuran), as identified by XRPD.

Figure 7:
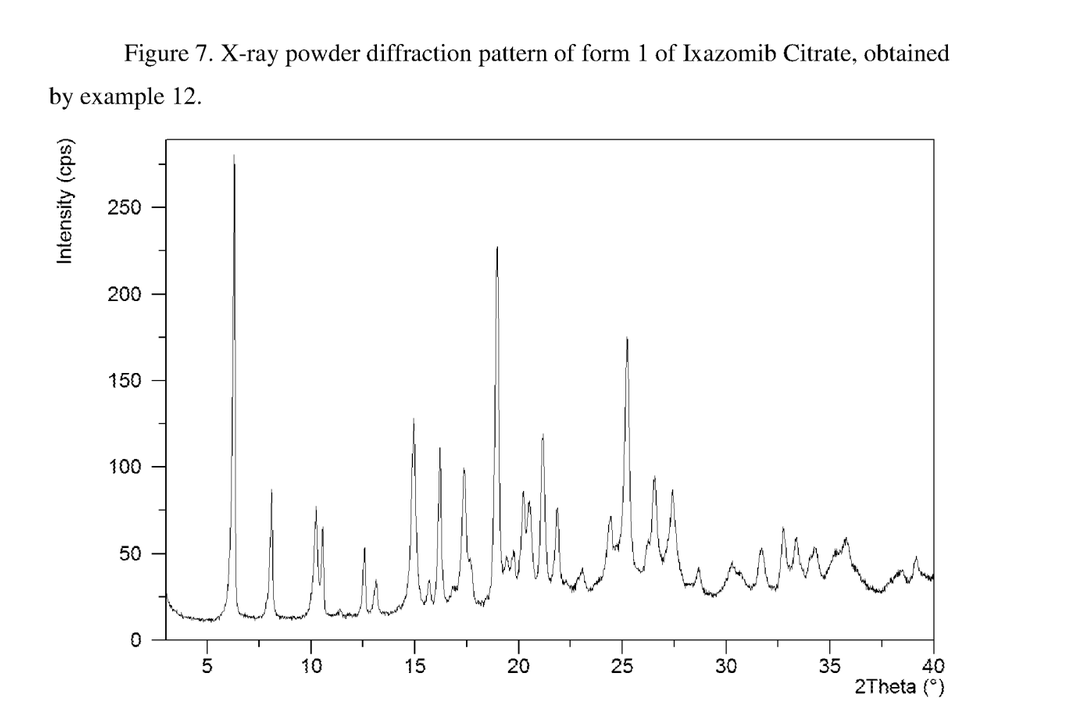
FIG. 7 shows the X-ray powder diffraction pattern of form 1 of Ixazomib Citrate, obtained by example 12.

Example 12. Preparation of Form 1 of Ixazomib Citrate Having Low Level of Residual Solvents Ixazomib citrate form 2 (5 g, 727 ppm of acetone, 1% of ethyl acetate, obtained by example 6) was dissolved in tetrahydrofuran (110 mL) at temperature about 40° C. Obtained solution was concentrated under reduced on rotary evaporator (pressure about 250 mbars and bath temperature about 44° C.) to about 10.6 g. Received viscous non-crystalline compound was dissolved in ethyl acetate (100 mL) at ambient temperature. The solution was seeded with suspension of Ixazomib Citrate form 1 (150 mg) at ambient temperature. After about 15 minutes of stirring at ambient temperature, the mixture was cooled during about 2 hours to about 0° C. and it was treated at about 0° C. for about 2.5 hours. Insoluble solid was separated by filtration and dried in an oven at temperature about 60° C. to give Ixazomib Citrate form1, free of form 2 (3.57 g, 125 ppm of residual ethyl acetate and 291 ppm of residual tetrahydrofuran), as identified by XRPD and the XRPD pattern is presented in FIG. 7.

The invention claimed is:

1. A process for preparation of Ixazomib Citrate comprising
   a) providing citric acid, a suitable ketone, optionally one or more solvents and compound 2:

Compound 2 wherein $R_1$ and $R_2$ taken together with the intervening oxygen and boron atoms, form an optionally substituted 5- to 10-membered ring having 0-2 additional ring heteroatoms selected from N, O, or S;
   b) adding a strong acid to afford Ixazomib Citrate; and
   c) optionally isolating Ixazomib Citrate; and wherein the reaction is performed in the absence of an organic boronic acid or boric acid acceptor.

2. The process according to claim 1 wherein $R_1$ and $R_2$ together form a chiral moiety.

3. The process according to claim 1 wherein the compound of formula 2 is— wherein $R_3$ and $R_6$ are each independently selected from the group consisting of hydrogen and $C_1$-$C_5$ alkyl; $R_4$ and $R_2$ taken together form an optionally substituted $C_5$-$C_7$ carbocycle, wherein the total number of carbon atoms is not more than 10.

4. The process according to claim 1 wherein the compound of formula 2 is 2,5-Dichloro-N-[2-[[(1R)-1-[(3aS,4S,6S,7aR)-hexahydro-3a,5,5-trimethyl-4,6-methano-1,3,2-benzodioxaborol-2-yl]-3-methylbutyl]amino]-2-oxoethyl]benzamide.

5. The process according to claim 1 wherein the suitable ketone is selected from the group consisting of $C_3$-$C_9$ ketones.

6. The process according to claim 1 wherein the suitable ketone is selected from the group consisting of $C_3$-$C_6$ ketones.

7. The process according to any one of claims 1-6 wherein the suitable ketone is acetone.

8. The process according to claim 1 wherein a pinanediol ketal is formed.

9. The process according to claim 1 wherein a pinanediol acetonide is formed.

10. The process according to claim 1 wherein the strong acid is HCl and the amount of HCl used in step (b) is less than an equimolar amount with respect to the amount of the starting material, i.e. compound 2.

11. The process according to claim 1 wherein steps a) and b) may be interchangeable or all the components provided in steps a) and b) may be provided together.

12. The process according to claim 1 wherein steps a) and b) are performed in acetone as a single solvent.

13. The process according to claim 1 wherein the process is a one-pot process.

14. The process according to claim 1 wherein the process is performed in a one phase system.

15. The process according to claim 1 wherein in step (c) Ixazomib Citrate is isolated by crystallization.

16. The process according to claim 1 wherein Ixazomib Citrate is characterized by any one of the following:
   i) having less than about 5000 ppm of acetone;
   ii) having less than about 5000 ppm of ethyl acetate;
   iii) having less than about 720 ppm of THF; and combinations of these data.

* * * * *